United States Patent
Eichler et al.

[11] Patent Number: 5,899,365
[45] Date of Patent: May 4, 1999

[54] DEVICE FOR ASSISTING MANUAL ACTUATION OF AN AEROSOL DISPENSER

[75] Inventors: Gerd Eichler, Seibersbach; Dieter Hochrainer, Bingen am Rhein; Reiner Reeg, Pforzheim, all of Germany

[73] Assignee: Boehringer Ingelheim KG, Ingelheim am Rhein, Germany

[21] Appl. No.: 08/817,355

[22] PCT Filed: Oct. 6, 1995

[86] PCT No.: PCT/EP95/03951

§ 371 Date: Sep. 20, 1997

§ 102(e) Date: Sep. 20, 1997

[87] PCT Pub. No.: WO96/11152

PCT Pub. Date: Apr. 18, 1996

[30] Foreign Application Priority Data

Oct. 10, 1994 [DE] Germany ............................ 44 36 051

[51] Int. Cl.⁶ ........................................................ B67D 5/64
[52] U.S. Cl. ........................................... 222/162; 222/509
[58] Field of Search ............................. 222/173, 162, 222/509

[56] References Cited

U.S. PATENT DOCUMENTS

| | | | |
|---|---|---|---|
| 3,272,392 | 9/1966 | Meshberg | 222/162 |
| 3,344,959 | 10/1967 | Faso | 222/162 X |
| 5,088,624 | 2/1992 | Hackett et al. | 222/509 X |

FOREIGN PATENT DOCUMENTS

| | | |
|---|---|---|
| 2671294 | 7/1992 | France . |
| 1097254 | 1/1968 | United Kingdom . |

*Primary Examiner*—Gregory L. Huson
*Attorney, Agent, or Firm*—Robert P. Raymond; Alan R. Stempel; Mary-Ellen Devlin

[57] ABSTRACT

A device for assisting the manual actuation of aerosol dispensers, especially dispensers of the sort used to dispense metered doses of phamaceuticals. Dispensers to be used with the device of the invention are of known per se design and comprise a container, a nozzle and a valve with an axially movable valve stem which releases material from the container when the valve stem is urged toward the container. Such dispensers are normally actuated by exerting compressive force along the axis of the dispenser, by squeezing the nozzle and one end of the container between the thumb and forefinger. The device of the invention works with such dispensers so that they may instead be actuated by exerting compressive force in a direction that is orthogonal to the axis of the dispenser, by squeezing the device between the fingers and the palm, a motion that is easier for certain individuals.

2 Claims, 2 Drawing Sheets

DEVICE FOR ASSISTING MANUAL ACTUATION OF AN AEROSOL DISPENSER

The invention relates to a device which makes it easier to dispense an aerosol dose from conventional aerosol containers.

Conventional containers comprising pharmaceutical preparations which dispense an aerosol upon use are generally known as "aerosol containers". These containers are filled with a fluid preparation pressurised at a pressure of several bar, of which a certain amount is released as a spray which, together with the air, forms the aerosol. The preparations themselves comprise a liquefied fuel gas or fuel gas mixture in which at least one active substance and, optionally, auxiliary agents may be dissolved or suspended.

Figure 1:
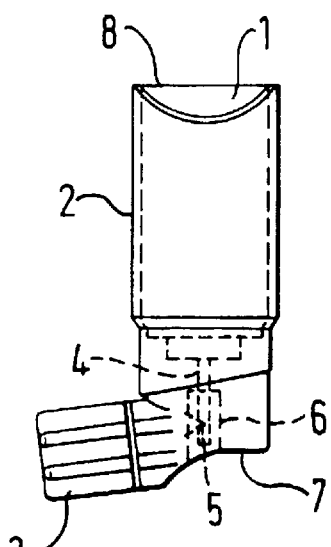
Figure 3:
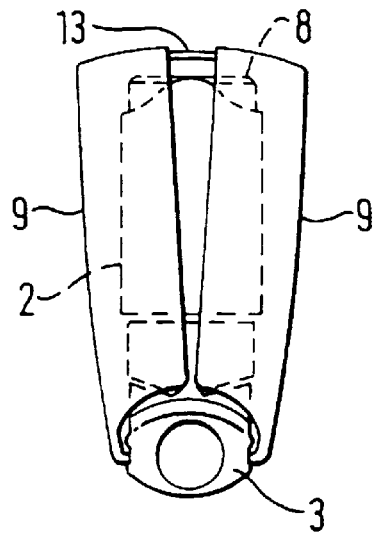
Figure 2:
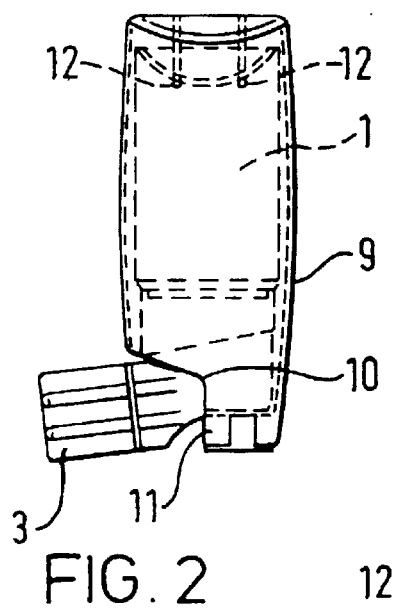
Figure 4:
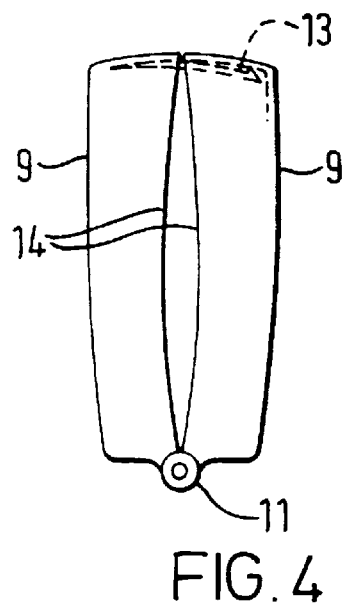
Figure 5:
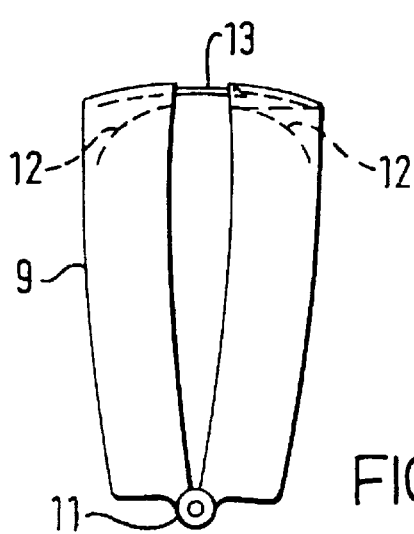
Figure 6:
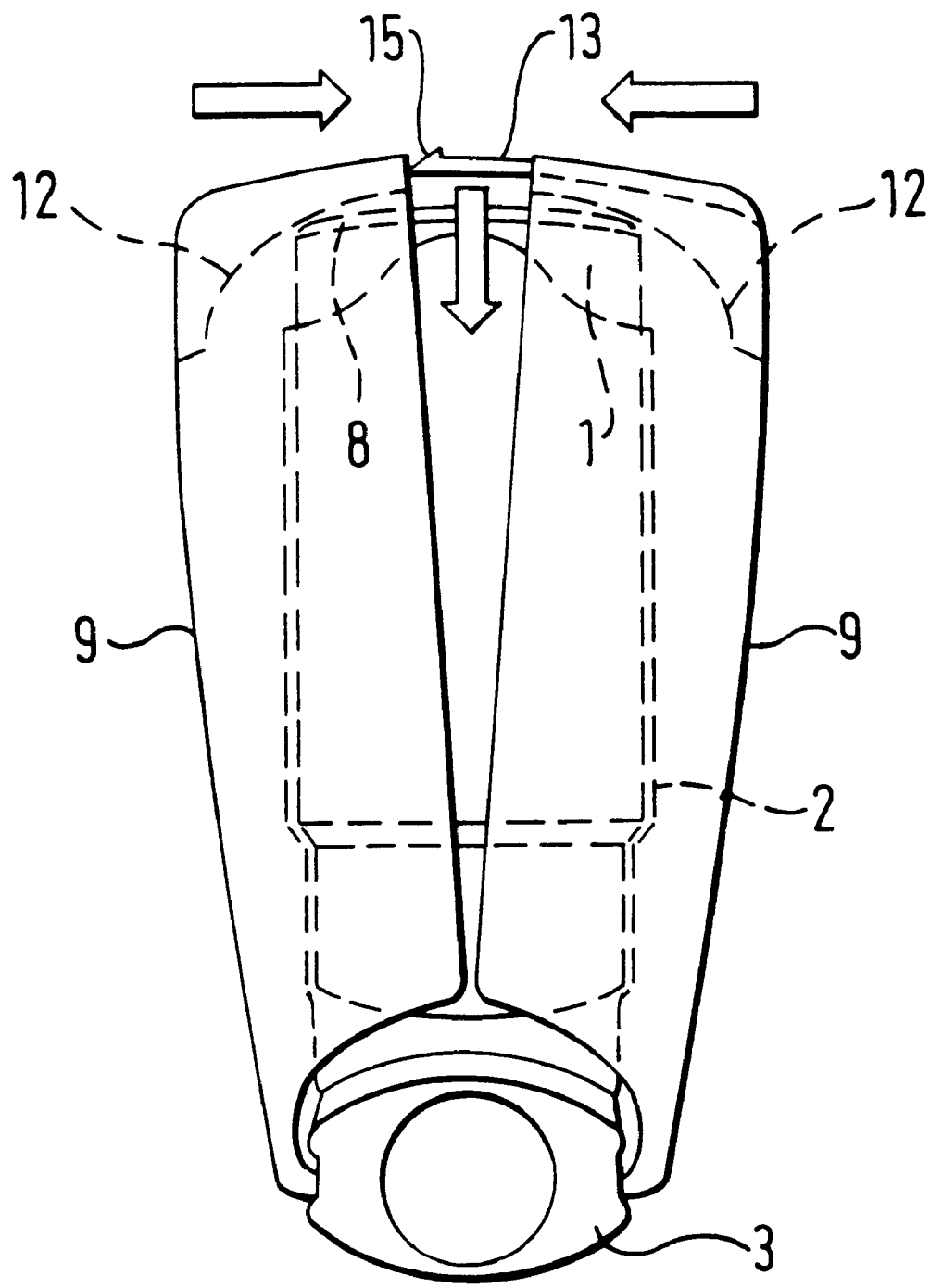

Conventional aerosol containers are provided with metering valves which dispense a fixed amount of the preparation during each operation. The release of the dose takes place when the axially movable valve stem of the metering valve is pressed in. In conventional equipment the valve stem is placed into a corresponding receiving means of a nozzle which simultaneously forms a support surface for the thumb or finger by means of which the valve stem is depressed. A typical aerosol container of this kind is shown in FIG. 1.

The aerosol container 1, while forming a lateral or cylindrical cavity, is positioned in a sleeve 2 open at the top, which is fixedly connected to the nozzle 3. The valve stem 4 with the lateral outlet orifice 5 is secured to the recess 6 of the nozzle. By means of the inner pressure of the container and a spring, the valve stem is pushed outwards. The forces acting thereon must be overcome to initiate an aerosol spray.

In order to actuate the container, the patient normally presses his thumb and one finger onto the grip surface 7 of the nozzle and onto the base 8 of the aerosol container. The initiation of the aerosol spray must be coordinated with the breathing of the patient so that the aerosol administration takes place at the right time during breathing in. It has been shown that many patients find this coordination difficult, for example, if there is a need for a particularly speedy administration in the event of an asthma attack. Here, it may happen that the patient administers too low a dose of active substance. If he himself has the feeling of having received an insufficient amount of active substance, he may possibly administer a further dose which could result in exceeding the proper dosage.

The device according to the invention described below is an accessory for conventional aerosol containers. It achieves the object of making release of the aerosol spray easier, thus also avoiding any problems of coordination.

The device of the invention largely comprises two elongate, shell-like members, whose open sides face one another. They are jointly able to receive a conventional aerosol dispenser with a nozzle and are, on one narrow side, pivotally connected by a hinge, the nozzle projecting through an opening close to the hinge, substantially perpendicular to the plane in which the pivotal movement takes place, and means being provided on the narrow side of the shell-like members positioned opposite the hinge. These means press onto the base of the aerosol container upon actuation of the device (thereby initiating an aerosol spray) and, upon non-actuation, under the pressure of the valve stem, cause the shell-like members to pivot away from one another in such a way that the valve stem reaches its starting position. The new device is surrounded by the whole hand and may therefore be triggered off in a particularly easy manner.

The invention is described in greater detail by means of a typical embodiment shown in FIGS. 2 to 6.

FIG. 2 is a lateral view of the device of the invention. Here, in the inside of the aerosol device, aerosol container 1, sleeve 2 and nozzle 3 are visible. The shell-like member 9, which is to the right in the operational position, faces the viewer. Hinge 11 is visible below opening 10 for nozzle 3. The means 12 are shaped in such a way that they increasingly push base 8 of the aerosol container downwards, while the shell-like members 9 are compressed. If the shell-like members 9 are then released, the forces acting upon the valve stem result in the valve stem being pushed out again into its starting position and the base 8 thus being pressed upwards. In this way, the shell-like members 9 are pivoted outwards so that the device may again be started.

FIG. 3 illustrates the embodiment shown in FIG. 2, during use. The shell-like members 9 are in their starting position. A tongue 13 ensures that the movable members 9 cannot be pivoted any further to the outside when the starting position is reached.

FIG. 4 shows the back of the device, in the end position upon actuation. The two shell-like members 9 come into contact on the side facing the hinge 11. Between the two members 9, there is a recess 14 limited by flat curved portions. They ensure that the skin of the patient's hand is not caught upon actuation. The recess may also be of another shape and may have a correspondingly shaped front.

FIG. 5 is also a view of the back of the device. However, it shows the starting position before actuation. The means 12 pressing onto the base 8 of the aerosol container are curved so that, upon compression of the two shell-like members 9, they slide over the edge of the base 8 and increasingly press it further downwards, thereby pushing the valve stem into the aerosol container until it reaches its end position.

FIG. 6 is a view of the front of the device, showing the frontal view of the nozzle 3 in the starting position before actuation. The tongue 13 with the barb 15 prevents the two shell-like members 9 from being opened out unintentionally. In this Figure, the tongue 13 is in the open position, i.e. before it engages in the shell part 9 positioned opposite. The Figure shows the coordinated action of the means 12 on the base 8 of the aerosol container 1 upon the pressing together of the two shell-like members 9.

The lateral arrangement of these two members 9 has proved to be particularly advantageous during use, because the hand is able to adopt a natural and relaxed position.

The shape of the individual members may be modified in various ways. The shell-like members 9 may, for example, be provided with overlapping parts so that there is no cavity even in the starting position (i.e. when the members 9 are pivoted apart). On the other hand, the shell-like members 9 may also be replaced by narrower members, provided there is sufficient rigidity, and/or they may have grip indentations. Furthermore, the skilled man has various possibilities of locking the device in the initial position so that it cannot be operated unintentionally.

The means 12 may also have other forms. In the Figures shown, they are shaped like narrow ribs with an arched boundary face which frictionally slides past the edge of the base of the aerosol container. Instead of being arched the sliding surface may also be of another suitable curved shape or, for example, be wedge-like. Furthermore, the hinge may be replaced by a connecting member made of flexible material. In order to illustrate the actuation process more clearly, the construction of the device may be such that a pressure point needs to be overcome before the aerosol spray is released. Finally, it is also possible to construct the device asymmetrically, so that the aerosol dispenser is fixedly arranged in the one shell-like member 9 and only the other shell-like member 9 is provided with a device 12 for depressing the aerosol container.

Preferably, the device of the invention is made of a sufficiently break-resistant plastic material.

What is claimed is:

1. A device for assisting manual actuation of an aerosol dispenser, wherein said aerosol dispenser is of the known per se type comprising:
   a) a cylindrical container having a first end, a second end, and a longitudinal axis;
   b) a metering valve having a valve stem with a fixed end and a free end, located at said first end of the container, which metering valve allows the release of material from the container, through the valve stem, when the valve stem is moved axially, by force directed toward said second end of the container; and,
   c) a nozzle having an inlet, into which the free end of the valve stem is inserted, a lateral outlet orifice, and a support surface;
   and wherein material is released from the container, through the lateral outlet orifice of the nozzle, when compressive force is exerted against the second end of the container and the support surface of the nozzle;
said device for assisting manual actuation of said aerosol dispenser comprising:
   a) two elongate, shell-like members, each having a first end and a second end, and each having an open side, the two members being spacially arranged such that the open sides face each other and define a space into which the aerosol dispenser may be received, with the first end of the container located proximate to the first ends of the shell-like members and the second end of the container located proximate to the second ends of the shell-like members;
   b) a hinge which joins the shell-like members at said first ends thereof and which permits said members to move toward and away from each other by pivotal motion about the hinge;
   c) at least one means, located on an open face of at least one of the two shell-like members, proximate to the second end thereof, for bearing against the second end of a container received between the two shell-like members when the two shell-like members are urged toward each other by manual pressure, and for thereby compressing the second end of the container and support surface of the nozzle between the first and second ends of the shell-like members, to thereby actuating the valve of the aerosol dispenser and release material from the container.

2. An improvement in an aerosol dispenser of the type comprising:
   a) a cylindrical container having a first end, a second end, and a longitudinal axis;
   b) a metering valve having a valve stem with a fixed end and a free end, located at said first end of the container, which metering valve allows the release of material from the container, through the valve stem, when the valve stem is moved axially, by force directed toward said second end of the container; and,
   c) a nozzle having an inlet, into which the free end of the valve stem is inserted, a lateral outlet orifice, and a support surface;
   and wherein material is released from the container, through the lateral outlet orifice of the nozzle, when compressive force is exerted against the second end of the container and the support surface of the nozzle;
wherein the improvement comprises the addition of a device for assisting manual actuation of said aerosol dispenser, wherein said device comprises:
   a) two elongate, shell-like members, each having a first end and a second end, and each having an open side, the two members being spacially arranged such that the open sides face each other and define a space into which the aerosol dispenser may be received, with the first end of the container located proximate to the first ends of the shell-like members and the second end of the container located proximate to the second ends of the shell-like members;
   b) a hinge which joins the shell-like members at said first ends thereof and which permits said members to move toward and away from each other by pivotal motion about the hinge;
   c) at least one means, located on an open face of at least one of the two shell-like members, proximate to the second end thereof, for bearing against the second end of a container received between the two shell-like members when the two shell-like members are urged toward each other by manual pressure, and for thereby compressing the second end of the container and support surface of the nozzle between the first and second ends of the shell-like members, to thereby actuating the valve of the aerosol dispenser and release material from the container.

* * * * *